United States Patent

Regnat et al.

[11] Patent Number: 5,600,006
[45] Date of Patent: Feb. 4, 1997

[54] BIS(DIARYLALKYL)PHOSPHINES

[75] Inventors: Dieter Regnat, Frankfurt; Hans-Jerg Kleiner, Kronberg, both of Germany

[73] Assignee: Hoechst A.G., Germany

[21] Appl. No.: 337,959

[22] Filed: Nov. 10, 1994

[30] Foreign Application Priority Data

Nov. 13, 1993 [DE] Germany .......................... 43 38 827.2
Sep. 19, 1994 [DE] Germany .......................... 44 33 294.7

[51] Int. Cl.$^6$ ...................................................... C07F 9/02
[52] U.S. Cl. ................................................ 568/16; 568/17
[58] Field of Search ........................................ 568/16, 17

[56] References Cited

U.S. PATENT DOCUMENTS

| | | | |
|---|---|---|---|
| 3,261,871 | 7/1966 | Fritzsche et al. | 568/17 |
| 4,824,977 | 4/1989 | Devon et al. | 568/17 |
| 4,851,581 | 7/1989 | Devon et al. | 568/17 |
| 4,956,055 | 9/1990 | Puckette | 568/17 |
| 5,012,002 | 4/1991 | Kumobayashi et al. | 568/17 |

OTHER PUBLICATIONS

Qu et al, Chem. Abst., vol. 115, # 159,270C (1991).
European Search Report, Dec. 30, 1994, No. 94117327.0.
Monatshefte Fur Chemie, vol. 124, 1993.
Chemical Abstracts, Band 91, Nr. 9, 27, Aug., 1979.

*Primary Examiner*—James H. Reamer
*Attorney, Agent, or Firm*—Connolly & Hutz

[57] ABSTRACT

The invention relates to novel 2,2'-bis [bis(aryl)phosphinomethyl]-1,1'-binaphthyls of the formula

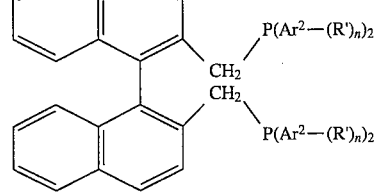

in which $Ar^2$ is a phenyl radical, R' is an alkyl radical having 1 to 4 carbon atoms, $CF_3$, fluorine, chlorine or bromine, and n is 1 or 2.

3 Claims, No Drawings

BIS(DIARYLALKYL)PHOSPHINES

The present invention relates to a process for preparing bis(diarylalkyl)phosphines and novel compounds from this class of substances.

Compounds containing two phosphino groups in the molecule (bidentate phosphine ligands) play an important role in a number of processes in which a transition metal complex is used as the catalyst. See also A. Miyashita et al. in Tetrahedron Lett. 34, (1993), 2351 and in J. Am. Chem. Soc. 102, (1980), 7932; R. Noyori et al., Tetrahedron 40, (1984), 1245; H. Takaya, Tetrahedron Lett. 34, (1993) 1615. Examples of such processes include hydrogenation, hydroformylation and carbonylation reactions or alkylation and arylation of aromatics.

One way of preparing bis(diarylalkyl)phosphines is to reduce the corresponding bis(diarylalkyl)phosphine oxides. Thus, it is known to reduce bis(diarylphosphinylalkyl)-1,1'-binaphthyls with trichlorosilane in a solvent to give bis(diarylphosphinoalkyl)-1,1'-binaphthyls. However, the yield is very low and is merely 30% in the case of 8,8'-bis(diphenylphosphinomethyl)-1,1'-binaphthyl [M. Widhalm, C. Kratky, Monatsh. f. Chemie 124, 103 (1993)]. Preparation of 2,2'-bis(diphenylphosphino-methyl)-1,1'-binaphthyl also gives a yield of only 30% [M. Kumada, JP 7939,059, CA 91 (1979) 91764v].

Another disadvantage is that the handling of trichlorosilane is associated with a risk potential owing to the ignition temperature of 185° to 200° C. Moreover, the reaction of phosphine oxides with trichlorosilane results in the formation of sublimates. These sublimates are probably due to siloxanes formed during the reaction from trichlorosilane. However, sublimates are highly undesirable because they lead to the formation of obstacles and blockages in lines, adapters and valves. For this reason they constitute a substantial risk for the working safety of the process. The reaction mixture formed after reaction of phosphine oxides with trichlorosilane is hydrolyzed with oxygen-free 20 to 30% aqueous sodium hydroxide solution. This removes the siloxanes obtained in solid form from the reaction mixture by dissolving, after which the organic phase freed from the siloxanes and containing the bis(diarylalkyl)phosphines can be separated from the aqueous phase. The bis(diarylalkyl)phosphines are isolated from the organic phase as crude products, after the solvent has been distilled off, and are then further purified by crystallization.

It is therefore a worthwhile object to develop a process which avoids the disadvantages described above. This object is achieved by a process for preparing bis(diarylalkyl)phosphines of the formula

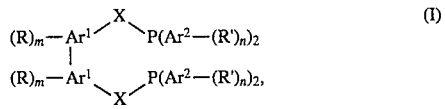

in which $Ar^1$ is a phenyl or naphthyl radical, $Ar^2$ is a phenyl or naphthyl radical, R and R' are in each case, independently of one another, identical or different and are H, an alkyl, alkoxy, aryloxy radical having 1 to 8 carbon atoms, a dialkylamino radical having 2 to 8 carbon atoms, F, Cl or Br, m is an integer from 1 to 4, n is an integer from 1 to 5, and X is an alkylene group having 1 to 3 carbon atoms. The process comprises reacting a bis(diarylalkyl)phosphine oxide of the formula

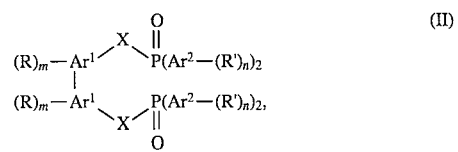

in which $Ar^1$, $Ar^2$, R, R', m, n and X have the above meaning, with an organodichlorosilane of the formula

in which R" is an alkyl or alkylene radical having 1 to 6 carbon atoms or an aromatic radical having 6 to 10 carbon atoms and k is an integer from 1 to 3, in the presence of a tertiary amine having a total of 6 to 24 carbon atoms at 80° to 220° C., if desired in the presence of a solvent.

Owing to the higher ignition temperatures of organodichlorosilanes, the process according to the invention has a lower risk potential and requires fewer safety precautions than in the case of using trichlorosilane. Thus, for example, methyldichlorosilane has a higher ignition temperature of 230° C., compared with trichlorosilane. Furthermore, methyldichlorosilane is stable in air while trichlorosilane ignites in air.

Moreover, surprisingly, no sublimates are formed in the reaction of bis(diarylalkyl)phosphine oxides of the formula (II) with organodichlorosilanes. Therefore there is no risk either that undesirable blockages of lines, adapters and valves endangering the working safety of the process will occur. In addition, the process according to the invention provides the desired value products in high yields (usually 80% and more).

The reaction mixture obtained after the reaction can be worked up by the method described previously in the prior art. However, surprisingly, it is also possible to do without this complicated kind of workup and to recover the value product in a simple manner without the need for carrying out a hydrolysis.

As mentioned above, the process according to the invention is suitable for reacting bis(diarylalkyl)phosphine oxides of the formula (II), in particular those in which $Ar^1$ is a naphthyl radical and/or $Ar^2$ is a phenyl radical.

Without claiming to be complete, the list of bis(diarylalkyl)phosphine oxides may include the following compounds:
2,2'-bis(diphenylphosphinylmethyl)-1,1'-binaphthyl,
2,3'-bis(diphenylphosphinylmethyl)-1,1'-binaphthyl,
4,4'-bis(diphenylphosphinylmethyl)-1,1'-binaphthyl,
8,8'-bis(diphenylphosphinylmethyl)-1,1'-binaphthyl,
2,2'-bis[(bis-1-naphthylphosphinyl)methyl]-1,1'-binaphthyl,
2,2'-bis[2-(diphenylphosphinyl)ethyl]-1,1'-binaphthyl and
2,2'-bis[3-(diphenylphosphinyl)propyl]-1,1'-binaphthyl.

Particularly suitable starting compounds are bis(diarylalkyl)phosphine oxides of the formula (II) in which R and R' are, in each case independently of one another, identical or different and are H, F, an alkyl radical, an alkoxy radical, each having 1 to 8, in particular 1 to 4, carbon atoms, and are in particular H, F or an alkyl radical, preferably H. As mentioned at the beginning, X is an alkylene group having 1 to 3 carbon atoms, in particular a methylene, dimethylene or trimethylene group, preferably a methylene or dimethylene group.

Reducing agents used are organodichlorosilanes of the formula (III), in particular those in which k is 1.

The following may be mentioned as a selection of suitable organodichlorosilanes:

methyldichlorosilane, ethyldichlorosilane, 1-propyldichlorosilane, 2-propyldichlorosilane, 1-butyldichlorosilane, 1-hexyldichlorosilane, 1,4-butylenebis-(dichlorosilane), phenyldichlorosilane and 1,4-phenylenebis(dichlorosilane).

The organodichlorosilane used is usually one of the formula (III) in which R" is an alkyl radical having 1 to 6, in particular 1 to 4, carbon atoms or a substituted or unsubstituted phenyl radical. Particularly suitable reducing agents are methyldichlorosilane, ethyldichlorosilane or phenyldichlorosilane, in particular methyldichlorosilane.

As mentioned above, the reaction is carried out in the presence of a tertiary amine.

Examples of suitable tertiary amines are tri-n-propylamine, tri-iso-propylamine, n-butyl-di-n-propylamine, di-n-butyl-n-propylamine, tri-n-butylamine, tri-iso-butylamine, di-n-butyl-ethylamine, n-propyl-n-butyl-n-pentylamine, di-n-propyl-n-pentylamine, di-n-pentyl-n-propylamine, tri-n-pentylamine, tri-n-hexylamine.

In a number of cases it has proven favorable to use, as the tertiary amine, a trialkylamine having a total of 6 to 24, in particular 9 to 15, carbon atoms, in particular tri-n-propyl-, tri-i-propyl-, tri-i-butyl-, tri-n-butyl and/or tri-n-pentylamine.

The reaction temperature at which the reaction is to be carried out depends to a certain extent also on the type and reactivity of the reactants used. Frequently it is sufficient to carry out the reaction at 90° to 180° C., in particular 100° to 160° C.

The reaction can be carried out in the presence or absence of a solvent. If a solvent is used, it is recommended that the solvent used be an aprotic solvent. Suitable aprotic solvents are toluene, o-xylene, m-xylene, p-xylene, technical mixtures of isomeric xylenes, mesitylene, chlorobenzene, dichlorobenzene, ethylbenzene, dioxane, acetonitrile, in particular toluene, a xylene, technical mixtures of isomeric xylenes, mesitylene, chlorobenzene, ethylbenzene, preferably toluene, a xylene or a technical mixture of isomeric xylenes. If desired, mixtures of these solvents can also be used.

The bis(diarylalkyl)phosphine oxide and the organodichlorosilane are usually used in a molar ratio of 1:2 to 1:10, in particular 1:4 to 1:6. In general, the organodichlorosilane and the tertiary amine are used in a molar ratio of 1:0.5 to 1:1.5, in particular 1:1 to 1:1.2.

The reaction can be carried out at atmospheric pressure or at superatmospheric pressure, in particular at the reaction pressure reached in each case.

As indicated above, the complicated workup described in the prior art can be avoided and the desired value product recovered from the reaction mixture in a simple manner. To this end, the solvent is distilled off directly from the reaction mixture obtained after the reaction 30, and the bis(diarylalkyl)phosphine is allowed to crystallize from the remaining reaction mixture dissolved in the tertiary amine. If it is desired to carry out this process variant, it is recommended that a tertiary amine be selected whose boiling point is significantly higher than that of the solvent used. When using toluene, xylene or ethylbenzene, tri-n-butylamine has proven to be a particularly useful tertiary amine.

The process according to the invention provides novel compounds of the formula (Ia)

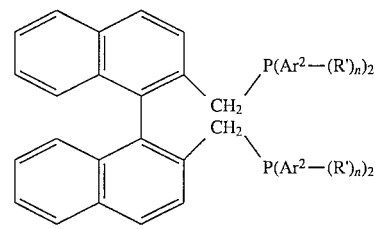

in which $Ar^2$ is a phenyl radical, R' is an alkyl radical having 1 to 6 carbon atoms, $CF_3$, fluorine, chlorine or bromine, in particular methyl, $CF_3$ or fluorine, and n is 1 or 2, in a surprisingly simple manner by reacting suitable 2,2'-bis-(diphenylphosphinylmethyl)-1,1'-binaphthyls (phosphine oxides of the formula (II) in which $(R)_m$—$Ar^1$—$Ar^1$—$(R)_m$ is a 1,1'-binaphthyl radical) with an organosilane of the formula (III).

Novel compounds falling under this definition are in particular the compounds 2,2'-bis[bis(2-fluorophenyl)phosphinomethyl]-1,1'-binaphthyl, 2,2'-bis[bis(3-fluorophenyl)phosphinomethyl]-1,1'-binaphthyl, 2,2'-bis[bis(4-fluorophenyl)phosphinomethyl]-1,1'-binaphthyl, 2,2'-bis[bis(2-methylphenyl)phosphinomethyl]-1,1'-binaphthyl, 2,2'-bis[bis(4-methyl phenyl)phosphinomethyl]-1,1'-binaphthyl, 2,2'-bis[bis(2trifluoromethylphenyl)phosphinomethyl]-1,1'-binaphtyl, 2,2'-bis[bis(4-trifluoromethylphenyl)phosphinomethyl]-1,1'-binaphthyl, 2,2'-bis[bis(2,3-difluorophenyl)phosphinomethyl]-1,1'-binaphthyl, 2,2'-bis[bis(2,4-difluorophenyl)phosphinomethyl]-1,1'-binaphthyl, 2,2'-bis[bis(3,5-difluorophenyl)phosphinomethyl]-1,1'-binaphthyl.

The examples which follow document the invention without limiting it.

EXPERIMENTAL SECTION

Example 1

Process for preparing 2,2'-bis(diphenylphosphinomethyl)-1,1'-binaphthyl using methyldichlorosilane:

409.7 g (0.6 mol) of 2,2'-bis(diphenylphosphinylmethyl)-1,1'-binaphthyl are suspended in 1.5 l of xylene and 715 ml (3.0 mol) of tri-n-butylamine in the absence of air and moisture, and 345.1 g (3.0 mol) of methyldichlorosilane are added dropwise with stirring. The mixture is then refluxed for 12 hours to give a clear solution. Xylene is distilled off at atmospheric pressure, and the mixture is allowed to cool with stirring. This results in the formation of 2,2'-bis(diphenylphosphinomethyl)-1,1'-binaphthyl as a colorless solid, which is filtered off under an inert gas and washed with 200 ml of degassed acetone. 378 g (97%) of colorless crystals of melting point 160° to 161° C. are obtained.

Example 2

Process for preparing 2,2'-bis(diphenylphosphinomethyl)-1,1'-binaphthyl using ethyldichlorosilane:

20.48 g (0.03 mol) of 2,2'-bis(diphenylphosphinylmethyl)-1,1'-binaphthyl are suspended in 80 ml of xylene and 39.3 ml (0.165 mol) of tri-n-butylamine in the absence of air and moisture, and 19.4 g (0.15 mol) of ethyldichlorosilane are added dropwise with stirring. The mixture is then refluxed for 13 hours to give a clear solution. Xylene is distilled off at atmospheric pressure, and the mixture is allowed to cool with stirring. This results in the formation of 2,2'-bis(diphenylphosphinomethyl)-1,1'-binaphthyl as a colorless solid, which is filtered off under an inert gas and washed with 20 ml of degassed acetone. 18.5 g (95%) of colorless crystals of melting point 160° to 161° C. are obtained.

Example 3

Process for preparing 2,2'-bis(diphenylphosphinomethyl)-1,1'-binaphthyl using phenyldichlorosilane:

20.48 g (0.03 mol) of 2,2'-bis(diphenylphosphinylmethyl)-1,1'-binaphthyl are suspended in 80 ml of xylene and 30.6 g (0.165 mol) of tri-n-butylamine in the absence of air and moisture, and 26.57 g (0.15 mol) of phenyldichlorosilane are added dropwise with stirring. The mixture is then refluxed for 13 hours to give a clear solution. Xylene is distilled off at atmospheric pressure, and the mixture is allowed to cool with stirring. This results in the formation of 2,2'-bis(diphenylphosphinomethyl)-1,1'-binaphthyl as a colorless solid, which is filtered off under an inert gas and washed with 20 ml of degassed acetone. 18.5 g (95%) of colorless crystals of melting point 160° to 161° C. are obtained.

Example 4

Process for preparing 8,8'-bis(diphenylphosphinomethyl)-1,1'-binaphthyl using methyldichlorosilane:

20.48 g (0.03 mol) of 8,8'-bis(diphenylphosphinylmethyl)-1,1'-binaphthyl are suspended in 75 ml of xylene and 36 ml (0.15 mol) of tri-n-butylamine in the absence of air and moisture, and 16.57 g (0.144 mol) of methyldichlorosilane are added dropwise with stirring. The mixture is then refluxed for 14 hours to give a clear solution. Xylene is distilled off at atmospheric pressure, and the mixture is allowed to cool with stirring. This results in the formation of 8,8'-bis(diphenylphosphinomethyl)-1,1'-binaphthyl as a colorless solid, which is filtered off under an inert gas and washed with 20 ml of degassed acetone. 16.7 g (87%) of colorless crystals of melting point 168° to 170° C. are obtained.

Example 5

Preparation of 2,2'-bis[bis(3-fluorophenyl)phosphinomethyl]-1,1'-binaphthyl using phenyldichlorosilane:

7.6 g (0.01 mol) of 2,2'-bis[bis(3-fluorophenyl)phosphinylmethyl]-1,1'-binaphthyl are suspended in 50 ml of o-xylene and 8,4 ml (33 mmol) of tributylamine in the absence of air and moisture, and 5.3 g (30 mmol) of phenyldichlorosilane are added dropwise with stirring. The mixture is then refluxed for 5 hours to give a clear solution. o-Xylene is distilled off at atmospheric pressure, and the reaction mixture is allowed to cool with stirring. This leads to the formation of a colorless solid, which is filtered off under inert gas and washed with 20 ml of degassed acetone to give 5.7 g (79%) of colorless crystals.

Melting point: 143° to 144° C.
$^{31}$P NMR: δ (CDCl$_3$)=−11.6 ppm

Example 6

Preparation of 2,2'-bis[bis(4-fluorophenyl)phosphinomethyl]-1,1'-binaphthyl using phenyldichlorosilane:

7.6 g (0.01 mol) of 2,2'-bis[bis(4-fluorophenyl)phosphinylmethyl]-1,1'-binaphthyl are suspended in 50 ml of oxylene and 8,4 ml (33 mmol) of tributylamine in the absence of air and moisture, and 5.3 g (30 mmol) of phenyldichlorosilane are added dropwise with stirring. The mixture is then refluxed for 5 hours to give a clear solution. o-Xylene is distilled off at atmospheric pressure, and the reaction mixture is allowed to cool with stirring. This leads to the formation of a colorless solid, which is filtered off under inert gas and washed with 20 ml of degassed acetone to give 5.9 g (82%) of colorless crystals.

$^{31}$P NMR: δ (CDCl$_3$)=−14.4 ppm

Example 7

Preparation of 2,2'-bis[bis(2-methylphenyl)phosphinomethyl]-1,1'-binaphthyl using phenyldichlorosilane:

18.0 g (0.0244 mol) of 2,2'-bis[bis(2-methylphenyl)phosphinylmethyl]-1,1'-binaphthyl are suspended in 150 ml of o-xylene and 21,7 ml (85 mmol) of tributylamine in the absence of air and moisture, and 13.3 g (73 mmol) of phenyldichlorosilane are added dropwise with stirring. The mixture is then refluxed for 24 hours to give a clear solution. o-Xylene is distilled off at atmospheric pressure, and the reaction mixture is allowed to cool with stirring. This leads to the formation of a colorless solid, which is filtered off under inert gas and washed with 20 ml of degassed acetone to give 12.6 g (73%) of colorless crystals.

Melting point: 105° to 107° C.
$^{31}$P NMR: δ (CDCl$_3$)=−35.6 ppm

What is claimed is:

1. A compound of the formula

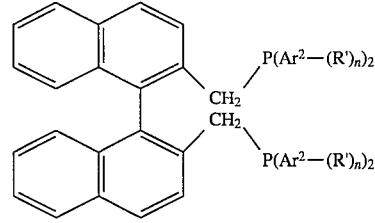

in which Ar$^2$ is a phenyl radical, R' is an alkyl radical having 1 to 4 carbon atoms, CF$_3$, fluorine, chlorine or bromine, and n is 1 or 2.

2. A compound of the formula

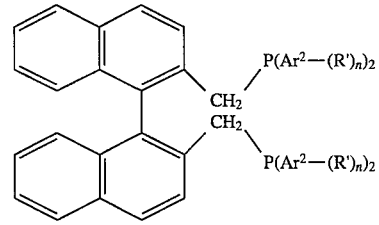

in which Ar$^2$ is phenyl, R' is methyl, CF$_3$ or fluorine, and n is 1 or 2.

3. The compounds 2,2'-bis[bis(2-fluorophenyl)phosphinomethyl]-1,1'-binaphthyl, 2,2'-bis[bis(3-fluorophenyl)phosphinomethyl]-1,1'-binaphthyl, 2,2'-bis[bis(4-fluorophenyl)phosphinomethyl]-1,1'-binaphthyl, 2,2'-bis[bis(2-methylphenyl)phosphinomethyl]-1,1'-binaphthyl, 2,2'-bis[bis(4-methylphenyl)phosphinomethyl]-1,1'-binaphthyl, 2,2'-bis[bis(2-trifluoromethylphenyl)phosphinomethyl]-1,1'-binaphthyl, 2,2'-bis[bis(4-trifluoromethylphenyl)phosphinomethyl]-1,1'-binaphthyl, 2,2'-bis[bis(2,3-difluorophenyl)phosphinomethyl]-1,1'-binaphthyl, 2,2'-bis[bis(2,4-difluorophenyl)phosphinomethyl]-1,1'-binaphthyl and 2,2'-bis[bis(3,5-difluorophenyl)phosphinomethyl]-1,1'-binaphthyl.

* * * * *